United States Patent [19]

Morisey

[11] Patent Number: 4,717,539

[45] Date of Patent: Jan. 5, 1988

[54] CORROSION RESISTANT ALLOYS

[75] Inventor: David P. Morisey, Concord, Calif.

[73] Assignees: Alma Phillips, Oakland; Hugh Finley, Piedmont, both of Calif. ; part interest to each

[21] Appl. No.: 854,995

[22] Filed: Apr. 22, 1986

Related U.S. Application Data

[63] Continuation of Ser. No. 701,300, Feb. 13, 1985, abandoned.

[51] Int. Cl.$^4$ .................. C22C 9/06; C22C 19/03; A61C 13/08
[52] U.S. Cl. .................. 420/457; 420/488; 420/489; 148/435; 148/442; 433/207
[58] Field of Search ............ 420/457, 488, 489, 490, 420/494, 495, 487; 148/414, 419, 435, 442, 400; 433/200, 207, 222

[56] References Cited

U.S. PATENT DOCUMENTS 2,430,306 11/1947 Smith .................. 420/488
4,481,030 11/1984 Schmidt et al. .................. 75/10.23

FOREIGN PATENT DOCUMENTS 56925 5/1979 Japan .................. 420/494

*Primary Examiner*—L. Dewayne Rutledge
*Assistant Examiner*—George Wyszomierski
*Attorney, Agent, or Firm*—Phillips, Moore, Lempio & Finley

[57] ABSTRACT

A group of alloys exhibiting good corrosion resistance and with properties suitable for fabricating dental prostheses consist essentially of copper, nickel and tantalum. Copper and nickel comprise the major components, while tantalum is present in lesser quantities. Lithium and/or Ce, Si metal may be added in small amounts as a deoxidant. Minor amounts of elements such as aluminum, gallium, indium, silicon, titanium and cerium can be added to modify the physical properties of the alloys.

13 Claims, No Drawings

CORROSION RESISTANT ALLOYS

This is a continuation of Ser. No. 701,300, filed Feb. 13, 1985, abandoned.

BACKGROUND OF THE INVENTION

Alloys used to fabricate articles such as dental protheses must withstand highly corrosive and complex environmental conditions. The fluids bathing the oral cavity possess many components that are capable of corroding alloys based on many normally corrosion resistant elements. These components comprise both organic salts and inorganic salts such as sodium chloride and potassium thiocyanate. Various digestive enzymes, organic fluids including proteins, mucin, serum albumin, globulins, and cellular material such as leucocytes and epithelial debris also make up the oral fluids. These materials are extraordinarily corrosive to a wide cross-section of alloy materials.

Since dental alloys are intended for prolonged use in conjunction with living tissues, they must also be free of toxic effects either when in direct contact with adjacent tissue; or if ingested when the alloy components are eroded or corroded by the oral fluids.

Since the advent of modern dental practices within the last 100 years, alloys based upon the noble metals, especially gold, silver, platinum and palladium have been the preferred metals from which dental protheses have been fabricated. The reason these metals have been so widely utilized resides in their qualities of relative inertness in the oral environment, lack of toxic effects, their ability to alloy with other metals to produce products with a broad range of properties such as ductility, ease of casting and burnishing, high strength, corrosion and tarnish resistance, and the like.

The principal drawback associated with the use of the aforesaid precious metals in such alloys resides in their increasingly higher cost. The cost of these precious metals has multiplied several times over in the past several decades, and it is anticipated that these costs will continue to escalate in the coming years.

Principally because of the high cost of the precious metals, but also because of a desire for prostheses of lighter weight and greater stiffness, alloys based upon cobalt and chromium, or nickel and chromium have gained wide acceptance. These Co-Cr or Ni-Cr alloys can be prepared with a wide range of properties, however they are most universally used in partial dentures and ceramic crowns and bridges. Nonetheless, these Co-Cr and Ni-Cr alloys tend to be quite hard and stiff, are difficult to grind, shape, and burnish after casting. These difficulties present a drawback to their use and accounts, in part, for their failure to fully supplant precious metal alloys.

For dental purposes, five types of alloys are generally recognized:

Type I are soft alloys exhibiting a Brinell hardness (Vickers Hardness) in the range of 40–75 (50–90). They can be easily burnished to yield good and exact margins. Such alloys are intended for inlay restorations of the simpler non stress-bearing types.

Type II alloys are medium-hard alloys exhibiting a Brinell hardness (Vickers) in the 70–100 (90–120) range. They are difficult to burnish, but can be heat treated. They are intended for use in moderate stress situations, i.e., as three quarter crowns, abutments, pontics, full crowns, and saddles.

Type III alloys are hard, strong and the least ductile of the cast-inlay alloys. These alloys exhibit Brinell hardness (Vickers) in the range of 90–140 (120–150) and cannot be burnished, they can be heat treated, but this reduces their ductility. They are used in high-stress applications in three quarter crowns, abutments, pontics, appliance supports and precision fitting inlays.

Type IV alloys are extra hard partial denture alloys used where high strength, great hardness and stiffness are required. They exhibit Brinell (Vickers) hardness in the range of 130–200 (150 and up) and are used for cast removable partial dentures, precision-cast fixed bridges, some three quarter crowns, saddles, bars, arches, and clasps.

Ceramic compatible alloys comprise the final type of dental alloys. These alloys are characterized by an ability to form strong high precision crowns and bridges coupled with an ability to strongly bond to dental ceramic materials and to withstand rupture of the alloy-ceramic bond under high stress.

Generally speaking, only the precious metal alloys can be produced to cover the entire range of alloy types, albiet with the addition of a wide range of alloying components to modify the alloy's properties for different applications. The Co-Cr and Ni-Cr alloys can be produced in a fairly wide range of properties. However they are not useful in Type I, II or III applications or where softer, more ductile alloys are needed.

There is a continuing need for alloy systems that have the versatility of the precious metal alloys, but with a cost approaching that of the Co-Cr and Ni-Cr alloys.

BRIEF DESCRIPTION OF THE INVENTION

The present invention relates to an alloy system that is adaptable to most uses to which dental alloys are put; which exhibit compatibility with the oral environment; and which are inherently less costly than the precious metal alloys.

More specifically, the alloys of the invention consist essentially of the elements copper, nickel, and tantalum. In some instances, small amounts of other elements may be added to adjust the alloy properties for different applications. As used hereinafter all percentages refer to percentage by weight.

Copper and nickel comprise the two major components of the alloys. Copper is considered to be the base upon which the alloys are built, it can be present in a range of from about 30% to about 83%. Nickel is considered to be the second component in the alloys, which it can be present in a range of from about 15% up to as high as 60%. Generally however, nickel is normally present in amounts up to 40%, with amounts above that figure being reserved for alloys having special applications where highly oxidizing or sulfide environments are anticipated. As will be noted hereinafter, in some alloy compositions the nickel percentage may exceed the copper percentage.

The third major component of the alloys is tantalum. Tantalum may be present in the range of from about 2 to 12%. Small amounts of a deoxidizing element, preferably lithium, approximately 0.05 to 0.25% are usually included during the alloy production process.

Other elements, e.g., gallium, indium, aluminum, silicon, titanium, cerium may be added in small amounts, perhaps up to 3%, to modify the properties of the basic Cu, Ni, Ta alloys for specific uses.

It is an object of the invention to provide a system of Cu, Ni, Ta based alloys.

It is a further object of the invention to provide Cu, Ni, Ta based alloys that have use in dental applications.

It is another object of the invention to provide Cu, Ni, Ta based alloys that can be used as crown, bridge, partial denture, and ceramic compatible alloys.

It is still another object of the invention to provide corrosion resistant alloys based upon Cu, Ni and Ta.

It is yet another object of the invention to provide Cu, Ni, Ta based alloys with small amounts of either Ga, In, Al, Ce, Ti, and/or Si added thereto to modify the properties of the basic alloys.

Other objects and advantages of the alloys will be apparent from a review of the following specification and claims appended hereto.

DETAILED DESCRIPTION OF THE INVENTION

The alloys of the invention are based upon Cu and Ni with smaller amounts of Ta included therein.

Cu and Ni form a continuous series of solid solutions so that their relative percentages can vary over the entire range of from 0–100%. However for the purposes of this invention, alloys having from about 30 up to about 83% Cu; and from about 15 up to about 60% Ni are contemplated. Small variations above or below these limits can be useful, however most applications will require Cu and Ni to be within the stated ranges.

The third major and basic component in the alloys is Ta. Tantalum is normally immiscible in copper; however, in this instance, the presence of nickel, in which tantalum is soluble, effectively permits the production of a single phase alloy. The presence of tantalum is critical to the desirable properties of the alloys, especially in respect to the high corrosion resistance exhibited in the presence of highly corrosive salts such as ferric chloride, sodium chloride and the like. Tantalum is present in the alloys in the range of from about 2 to about 12%.

The best physical and chemical properties of the alloys appear when the Ni to Ta ratios are maintained in the vicinity of 5 to 1. Thus if Ni is present at 30%, Ta should be present at about 6%. Similarily, if Ni is present at about 40%, then Ta should be maintained at about 8%. While the above Ni/Ta ratios are most desirable, it should be understood that for some purposes the Ni/Ta ratio may alter considerably from the most desirable ratio.

For use as Type III and Type IV dental alloys, the preferred alloy compositions have about 30–40% Ni, 5–8% Ta, with Cu as the remainder. Where the alloys are to be utilized in conjunction with ceramics some departure from the above preferred percentages is desirable. For the ceramic compatible alloys, Ni may be increased up to about 60% and Ta reduced to about 2%. At the same time, additions of about 5% Al, and about 0.5% Ga, yield alloys having good adherence to dental porcelain. Small additions of up to 1% of cerium to the above ceramic compatible alloys also improves ceramic bonding.

Where Type III, i.e., crown and bridge alloys are desired, the basic alloys may be modified to improve ductility and elongation. The addition of perhaps 0.25 to about 3% of either gallium and/or indium to the alloys produces these desired properties.

Where Type IV, i.e., partial denture alloys, are desired, the basic alloys may be modified to improve their strength and increase their modulus of elasticity. For this purpose it is desirable to add some aluminum and/or silicon. The addition of Al up to about 10% continually increases strength. The addition of up to about 3% Si does the same. A preferred composition for Type IV alloy is Ni 33%, Ta 6%, Al 1%, Si 1%, with Cu the remainder.

For the alloys of the invention it is most usually advantageous to add up to about 0.25% of lithium for the purposes of deoxidizing the alloy melt. In most instances, small residual amounts of Li will remain in the alloy when it is cast. These residual amounts of Li are beneficial to casting fluidity, producing solid complete castings. It will be understood that all of the various alloys and their variations discussed herein may include these small amounts of Li. It is to be understood that small amounts of other deoxidizing elements, e.g., cerium, silicon, may be used in place of lithium. Another advantage of including small amounts of lithium, cerium or silicon, resides in their ability to combine with any carbon in the alloy melt and to precipitate the same. It is undesirable to have any Ta carbides present in the alloys and the deoxidizing agents effectively prevent the inclusion of these carbides in the alloys.

As noted above, Ta is not normally soluble in Cu. Therefore it is necessary in the production of the alloys to follow special procedures to overcome this incompatibility. More specifically, the following is a procedure for producing a typical alloy having 63.9% Cu, 30% Ni, 6% Ta, and 0.1% Li:

The raw components comprise Cu metal, Ni metal, Ta metal, commercial Cu 90-Ni10 alloy, and commercial Cu 96-Li4 alloy. A non carbon crucible must be used. Refractory ceramic crucibles are quite suitable for this purpose. It is also desirable to prepare the alloy under an inert atmosphere.

To prepare 100 units of alloy, 23.2 units of Ni metal and 6 units of Ta metal are first charged into the alloying crucible. In separate addition buckets are placed 68 units of the Cu-Ni alloy, 0.3 units Cu metal, and 2.5 units of the Cu-Li alloy. The crucible is placed into a sealed furnace, the furnace is closed and then evacuated to about 1 micron pressure. The vacuum system is then valved off and the furnace chamber backfilled with Argon to about 1 atmosphere pressure.

Power is then applied to the furnace and the temperature is increased until the Ni and Ta melt and alloy together. Power is then turned off or reduced and the melt is permitted to cool to approximately 1000° C. At this point the Cu-Li alloy is added to the melt and power is reapplied. The Cu-Ni alloy is then added, followed by addition of the Cu metal itself. Power application is continued until melting of all added components is complete and alloying has taken place. The melt is then ready for pouring into a suitable mold.

In the event minor amounts of other elements are to be added, the addition is made at a point appropriate to their particular melting points and/or their solubilities in Cu, Ni or Ta.

The cast alloys are handled and prepared with the same general procedures used for precious metal alloys which are put to similar use.

The corrosion resistance of a number of the present alloys was tested using Part 31-ASTM Standard G31-72 entitled "Recommended Practice for Laboratory Immersion Corrosion Testing of Metals". This test is indicative of the alloys' abilities to withstand corrosion in a highly corrosive environment. Table I below presents the results of these corrosion tests:

TABLE I

| COMPOSITION | MILS PER YEAR CORROSION IN 10 WEIGHT PERCENT FeCl$_3$ |
|---|---|
| CuNi30Ta6Ga2Li .15 | 2790 |
| CuNi30Ta6Ga1Li .15 | 2216 |
| CuNi33Ta6In1Li .10 | 2747 |
| CuNi33Ta6AlSi1 | 2958 |
| CuNi25Ta5Al5Li .10 | 1890 |
| CuNi30Ta6Al5Li .15 | 2002 |
| NiCu35Ta2Al5Ga .25Ce .10Li .10 | 1923 |
| NiCu35Ta2Al5Ga .25Ce .50 | 2033 |
| NiCu35Ta2Al4Ga .50Li .10 | 1971 |

Hardness tests were conducted on some other samples of the alloys. Table II below presents the results:

TABLE II

| COMPOSITION | VICKERS HARDNESS 0.5 Kg LOAD |
|---|---|
| CuNi30Ta6Ga2Li .15 | 162 |
| CuNi30Ta6Ga1Li .15 | 134 |
| CuNi33Ta6In1Li .10 | 199 |
| CuNi33Ta6AlSi1 | 252 |
| CuNi25Ta5Al5Li .10 | 287 |
| CuNi30Ta6Al5Li .15 | 330 |
| NiCu35Ta2Al5Ga .25Ce .10Li .10 | 328 |
| NiCu35Ta2Al5Ga .25Ce .50 | 287 |
| NiCu35Ta2Al4Ga .50Li .10 | 199 |

Alloys of the invention intended for use with porcelain were tested for porcelain compatibility. A porcelain adhesion test was performed as follows: Dental porcelain was applied to a test strip and subsequently bent in a jig until failure of the bonded porcelain occurred. The amount and distribution of porcelain remaining was compared at 45 power magnification to a commercial base metal which exhibits excellent adhesion with dental porcelain. Alloys are rated, by comparison, as less, equal or more adherent to the porcelain. Table III below lists three alloys of the invention that exhibited better adhesion to porcelain than the commercial porcelain alloy.

TABLE III

| NiCu35Ta2Al5Ga .25Ce .10Li .10 | more |
|---|---|
| NiCu35Ta2Al5Ga .25Ce .50 | more |
| NiCu35Ta2Al4Ga .50Li .10 | more |

Although the description of the invention alloys has been directed to their utilization for dental prostheses, it should be apparent that the alloys have uses in other fields where high corrosion resistance, good ductility, and hardness is needed. For instance, marine or chemical piping and other marine or chemical equipment is a suitable area wherein these alloys will find use. Other related uses needing these same qualities are intended to be covered by this disclosure.

What I claim is:

1. As compositions of matter, alloys consisting essentially of about 41 to 65 percent by weight copper, about 30 to 33 percent by weight nickel, about 5 to 6 percent by weight tantalum, and about 0.05 to 0.25 percent by weight lithium.

2. A Type III dental alloy consisting essentially of about 30-40 weight percent nickel, about 5-8 weight percent tantalum, about 0.25-3 weight percent gallium or indium, about 0.05-0.25 weight percent lithium and the remainder copper.

3. A Type IV dental alloy consisting essentially of about 30-33 weight percent nickel, about 5-6 weight percent tantalum, up to about 10 weight percent aluminum, up to about 3 weight percent silicon, about 0.05-0.25 weight percent lithium, and the remainder copper.

4. A dental ceramic compatible alloy consisting essentially of about 60 weight percent nickel, about 2 weight percent tantalum, about 5 weight percent aluminum, about 0.5 weight percent gallium, up to 1 weight percent cerium, up to 0.25 weight percent lithium, and the remainder copper.

5. A dental prosthesis at least partly fabricated from an alloy consisting essentially of copper, nickel, tantalum, one of the group consisting of of galium or indium, and a deoxidant chosen from the group consisting of lithium, cerium or silicon.

6. As a composition of matter, ductile alloys consisting essentially of copper, nickel, and having between 2 and 12% by weight of tantalum, and at least 0.05 by weight of a deoxidizing element, said alloys formed in an inert environment by first melting tantalum with nickel and separately melting copper with the deoxidizing agent, then adding the copper-deoxidizing agent melt to the nickel-tantalum melt followed by adding metallic gallium.

7. The compositions of claim 6 wherein the deoxidizing element is lithium or cerium or silicon.

8. The compositions of claim 6 wherein copper is present in an amount of from about 30 to about 83 percent by weight, nickel is present in an amount of from about 15 to about 60 percent by weight, and tantalum is present in an amount of from about 2 to about 8 percent by weight.

9. The compositions of claim 4 wherein the deoxidzing element is lithium present in an amount of from about 0.05 to about 0.25 percent by weight.

10. The compositions of claim 6 further including minor amounts of an element selected from the group consisting of gallium, indium, aluminum, silicon, titanium, cerium, and mixtures of the same.

11. The compositions of claim 10 wherein the minor elements are present in an amount of up to 10 percent by weight.

12. The composition of claim 6 wherein following the step of melting the tantalum and nickel, the process includes allowing the nickel-tantalum melt to cool to about 1000° C. before adding the copper-deoxidizing element melt.

13. The composition of claim 12 further including the step of melting copper with nickel simultaneously with the nickel-tantalum and copper-deoxidizing element melts and also including the step of adding the second copper-nickel melt to the tantalum-nickel melt after the nickel-tantalum melt is allowed to cool to about 1000°.

* * * * *

UNITED STATES PATENT AND TRADEMARK OFFICE
CERTIFICATE OF CORRECTION

PATENT NO. : 4,717,539
DATED : January 5, 1988
INVENTOR(S) : David P. Morisey

It is certified that error appears in the above-identified patent and that said Letters Patent is hereby corrected as shown below:

COLUMN 6, LINE 22, AFTER "OF" DELETE --OF--.

COLUMN 6, LINE 27, AFTER "0.05" INSERT --%--.

COLUMN 6, LINE 42, DELETE "4" AND INSERT --8--.

Signed and Sealed this

Seventh Day of June, 1988

Attest:

DONALD J. QUIGG

*Attesting Officer*   Commissioner of Patents and Trademarks